US011002668B2

(12) United States Patent
Sangwai et al.

(10) Patent No.: US 11,002,668 B2
(45) Date of Patent: *May 11, 2021

(54) SYSTEMS AND METHODS FOR SCREENING SOLVENTS FOR DISSOLVING TANK BOTTOM SLUDGE

(71) Applicants: INDIAN INSTITUTE OF TECHNOLOGY MADRAS, Chennai (IN); OIL INDIA LIMITED, Duliajan (IN)

(72) Inventors: Jitendra Sangwai, Chennai (IN); Ramesh Gardas, Chennai (IN); Sivabalan Sakthivel, Chennai (IN); Sugirtha Velusamy, Chennai (IN); Srinivasan V Raju, Duliajan (IN); Prashant Dhodapkar, Duliajan (IN)

(73) Assignees: INDIAN INSTITUTE OF TECHNOLOGY MADRAS, Chennai (IN); OIL INDIA LIMITED, Duliajan (IN)

(*) Notice: Subject to any disclaimer, the term of this patent is extended or adjusted under 35 U.S.C. 154(b) by 11 days.

This patent is subject to a terminal disclaimer.

(21) Appl. No.: 16/414,201

(22) Filed: May 16, 2019

(65) Prior Publication Data

US 2020/0363325 A1 Nov. 19, 2020

Related U.S. Application Data

(62) Division of application No. 15/037,606, filed as application No. PCT/IB2014/066097 on Nov. 17, 2014, now Pat. No. 10,330,662.

(30) Foreign Application Priority Data

Nov. 18, 2013 (IN) ............................ 5300/CHE/2013
Dec. 13, 2013 (IN) ............................ 5805/CHE/2013

(51) Int. Cl.
*G01N 21/33* (2006.01)
*G01N 21/35* (2014.01)
(Continued)

(52) U.S. Cl.
CPC ............. *G01N 21/33* (2013.01); *G01N 21/35* (2013.01); *G01N 24/08* (2013.01); *G01N 33/2823* (2013.01)

(58) Field of Classification Search
CPC ........ G01N 21/33; G01N 21/35; G01N 21/31; G01N 21/25; G01N 24/08; G01N 24/00; G01N 33/2823; G01N 33/28; G01N 33/26
(Continued)

(56) References Cited

U.S. PATENT DOCUMENTS

2012/0048783 A1* 3/2012 Painter .................. C10G 1/045
208/390

FOREIGN PATENT DOCUMENTS

WO WO-2015071881 A1 * 5/2015 ......... G01N 33/2823

OTHER PUBLICATIONS

Sakthivel, Experimental Investigation on the Effect of Aliphatic Ionic Liquids on the Solubility of Heavy Crude Oil Using UV-Visible, Fourier Transform-Infrared, and 13C NMR Spectroscopy, Energy Fuels, 2014, 28, 6151-6162. (Year: 2014).*

(Continued)

*Primary Examiner* — Christine T Mui
(74) *Attorney, Agent, or Firm* — Convergence Intellectual Property Law P.C; Jonathan Garfinkel

(57) ABSTRACT

A method of screening solvents for the solubilization of petroleum hydrocarbons is disclosed. The method includes dissolving petroleum hydrocarbons in a selected solvent to form a first solution, adding an ionic liquid to the first solution and blending to form a second solution and measuring absorbance of the second solution using spectroscopic techniques. The solubilization of petroleum hydrocarbons in the solvent is then determined based on the difference between the measured absorbance of the first and (Continued)

second solution. A system for screening solvents for the solubilization of petroleum hydrocarbons is also disclosed. The system can be used in removal of wax deposition in refinery process equipment, process flow lines, during piping operations, up-gradation of wax, prevention of clogging of pipelines, processing of sludge or for removing sludge from petroleum tank installations and enhancing the crude oil flow.

7 Claims, 10 Drawing Sheets

(51) Int. Cl.
*G01N 24/08* (2006.01)
*G01N 33/28* (2006.01)

(58) Field of Classification Search
USPC .......................................................... 208/200
See application file for complete search history.

(56) References Cited

OTHER PUBLICATIONS

Li et al, Ionic Liquid Enhanced Solvent Extraction for Bitumen Recovery from Oil Sands, Energy Fuels, 2011, 25, 5224-5231. (Year: 2011).*

International Preliminary Report on Patentability for PCT/IB2014/066097, dated May 24, 2016, pp. 1-9. (Year: 2016).*

* cited by examiner

SYSTEMS AND METHODS FOR SCREENING SOLVENTS FOR DISSOLVING TANK BOTTOM SLUDGE

CROSS-REFERENCES TO RELATED APPLICATIONS

This application is a divisional application of U.S. application Ser. No. 15/037,606, entitled "SYSTEMS AND METHODS FOR SCREENING SOLVENTS FOR DISSOLVING TANK BOTTOM SLUDGE", filed on May 16, 2016, which is a 35 U.S.C. § 371 national stage filing of PCT Patent Application Number PCT/M2014/066097, filed Nov. 17, 2014, which claims priority to Indian provisional patent applications 5300/CHE/2013 entitled "FORMULATIONS FOR DISSOLUTION OF PETROLEUM SLUDGE OR WAXES AND METHOD FOR EVALUATION THEREOF" filed on Nov. 18, 2013 and 5805/CHE/2013 entitled "METHOD OF SCREENING SOLVENTS FOR DISSOLVING TANK BOTTOM SLUDGE" filed on Dec. 13, 2013, which are incorporated herein by reference.

FIELD OF THE INVENTION

Present disclosure relates generally to a method of screening solvents for dissolving petroleum hydrocarbons and in particular to the use of environmental friendly green solvents-ionic liquids for the dissolution of petroleum tank-bottom sludge (TBS).

DESCRIPTION OF THE RELATED ART

"Crude oil" refers to untreated or unrefined oil recovered from beneath the surface of the earth. Contaminants such as solids, heavy hydrocarbon fractions, as well as rust and scale from the piping and tank walls, that accumulate at the bottom of the oil tanks during crude oil processing/storage, are generally known as tank bottoms or tank bottom sludge (TBS). The build-up of TBS accelerates corrosion within the tank, affects tank maintenance, and reduces the working capacity of the tank, and hence need to be disposed of.

Disposal or removal of sludge has been a laborious procedure experienced by most of the oilfield operators and refineries worldwide, as these are poorly soluble. Conventional methods for the sludge disposal include manual cleaning of the sludge, injection of high pressure hot water or use of rotating tools. However, the manual cleaning methods are unsafe, costly, time consuming and cumbersome, and are not always employable in a hazardous environment.

The most common cleaning processes other than manual cleaning are crude oil washing (COW) and chemical cleaning. In some cases, the sludge is chemically treated and allowed to stand for specific period so as to get separated by gravity in a separate vessel. Specially designed mobile filter presses and centrifuges have been used for more cleaner and rapid separations. Due to the viscous nature and paraffinic/naphthenic composition of sludge, it is difficult to pump it out of the tanks. Use of dispersants to break the sludge into coarse material, and mixing the sludge with light crude oil has been tried in the art.

One effective way to process TBS is to dissolve the sludge in chemical solvents such as aromatic and aliphatic hydrocarbon liquids followed by cleaning. However, because of the complex nature of the sludge, the poor solubility and variable composition, solubilizing the sludge is a challenging task. It is therefore important to measure the solubility of TBS in a wide range of solvents so that an ideal solvent or solvent mixture could be identified. A simple method of measuring the solubility of a substance is to incrementally add the substance in a known volume of solvent till saturation is attained and measuring the amount of substance added. However, this can be time-consuming using conventional systems and methods.

The invention addresses some of the drawbacks of conventional methods and satisfies the need for a method and a system that measures solubility of petroleum hydrocarbons in a wide range of solvents and co-solvents, with further related advantages as set forth here.

SUMMARY OF THE INVENTION

Methods and systems for screening solvents for solubilization of petroleum hydrocarbons are disclosed.

In one embodiment, a method of screening solvents for processing petroleum hydrocarbons is disclosed, wherein petroleum hydrocarbons is dissolved in a selected solvent to form a first solution, to which a co-solvent, such as an ionic liquid is added to form a second solution. The absorbance of the first and second solution is measured using spectroscopic techniques. The efficacy of the ionic liquid in solubilizing petroleum hydrocarbons is determined based on the difference between the absorbance of the first and the second solutions. The above process is repeated using a plurality of solvents, ionic liquids or mixtures thereof.

In one aspect, the absorbance of the first and second solution is measured using UV-Vis spectroscopy, Fourier transform-infrared spectroscopy (FT-IR) or $^{13}$C-nuclear magnetic resonance (NMR).

In one aspect, the solvent is chosen from aromatic hydrocarbon solvents or aliphatic hydrocarbon solvents such as pentane, hexane, heptane, octane, decane, ethyl acetate benzene, ethyl benzene, xylene, phenol, toluene, and mixtures thereof.

In another aspect, the ionic liquid is chosen from 1,3-dimethylimidazolium 1,1,1-trifluoro-N-[(trifluoromethyl)sulfonyl]methanesulfonamide; 1-butyl-1-methyl-pyrrolidinium 1,1,1-trifluoro-N-[(trifluoromethyl)sulfonyl]methanesulfonamide; diethylammonium phosphate; diethylammonium sulfate; triethylammonium phosphate; triethylammonium sulfate; tripropylammonium sulfate; tributylammonium sulfate; 1-butyl-3-methylimidazolium 1,1,1-trifluoro-N-[(trifluoromethyl)sulfonyl]methanesulfonamide; 1-butyl-3-methylimidazolium chloride; 1-butyl-3-methyl imidazoliumhexafluorophosphate; 1-ethyl-3-methylimidazolium ethyl sulfate; 1-hexyl-3-methylimidazolium hexafluoro-phosphate; 1-decyl-3-methylimidazolium bis(trifluoromethylsulfonyl) imide; 1-octyl-3-methylimidazolium chloride; 1-hexyl-3-methylimidazolium hydrogen sulfate; triethyl-ammoniumtetrafluoroborate; triethylammonium acetate; or mixtures thereof.

In one other aspect, the petroleum hydrocarbon source is petroleum tank bottom sludge (TBS) or heavy crude oil. In another aspect, the efficiency of the method of solubilizing petroleum hydrocarbons is at least about 70%.

In another embodiment, a system for screening solvents for solubilizing petroleum hydrocarbons is disclosed. The system comprises a petroleum hydrocarbon source, one or more solvent sources, one or more ionic liquid sources, a mixing device for mixing petroleum hydrocarbons with said solvent or said ionic liquid, a sensor to determine spectroscopic absorbance of the solvent mixture, and a control module coupled to the sensor. The control module is configured to determine the solubilization of petroleum hydrocarbons in the solvent based on the absorbance.

In one other embodiment, a method of processing petroleum hydrocarbons is disclosed. The method comprises dissolving petroleum hydrocarbons in a selected solvent to form a first solution whose absorbance is measured using spectroscopic techniques, subsequently adding an ionic liquid into the first solution to form a second solution. The absorbance of the second solution is then measured, and solubilization of petroleum hydrocarbons in the solvent is then calculated based on the difference between the absorbance of the first and the second solutions. The process is repeated for a plurality of solvents and ionic liquids so that at least one solvent and one ionic liquid can be selected based on the solubilization values. The petroleum hydrocarbon is then processed using the selected solvent and the ionic liquid in combination.

In one aspect, the method further comprises performing hold-time study for the selected solvent and ionic liquid combination to determine the efficiency of the petroleum hydrocarbon solubilization, wherein the solubilization percent of petroleum hydrocarbons is found to be between 60% and 230%.

BRIEF DESCRIPTION OF THE DRAWINGS

The invention has other advantages and features which will be more readily apparent from the following detailed description of the invention and the appended claims, when taken in conjunction with the accompanying drawings, in which:

Referring to the drawings, like numbers indicate like parts throughout the views.

DETAILED DESCRIPTION

Figure 1:
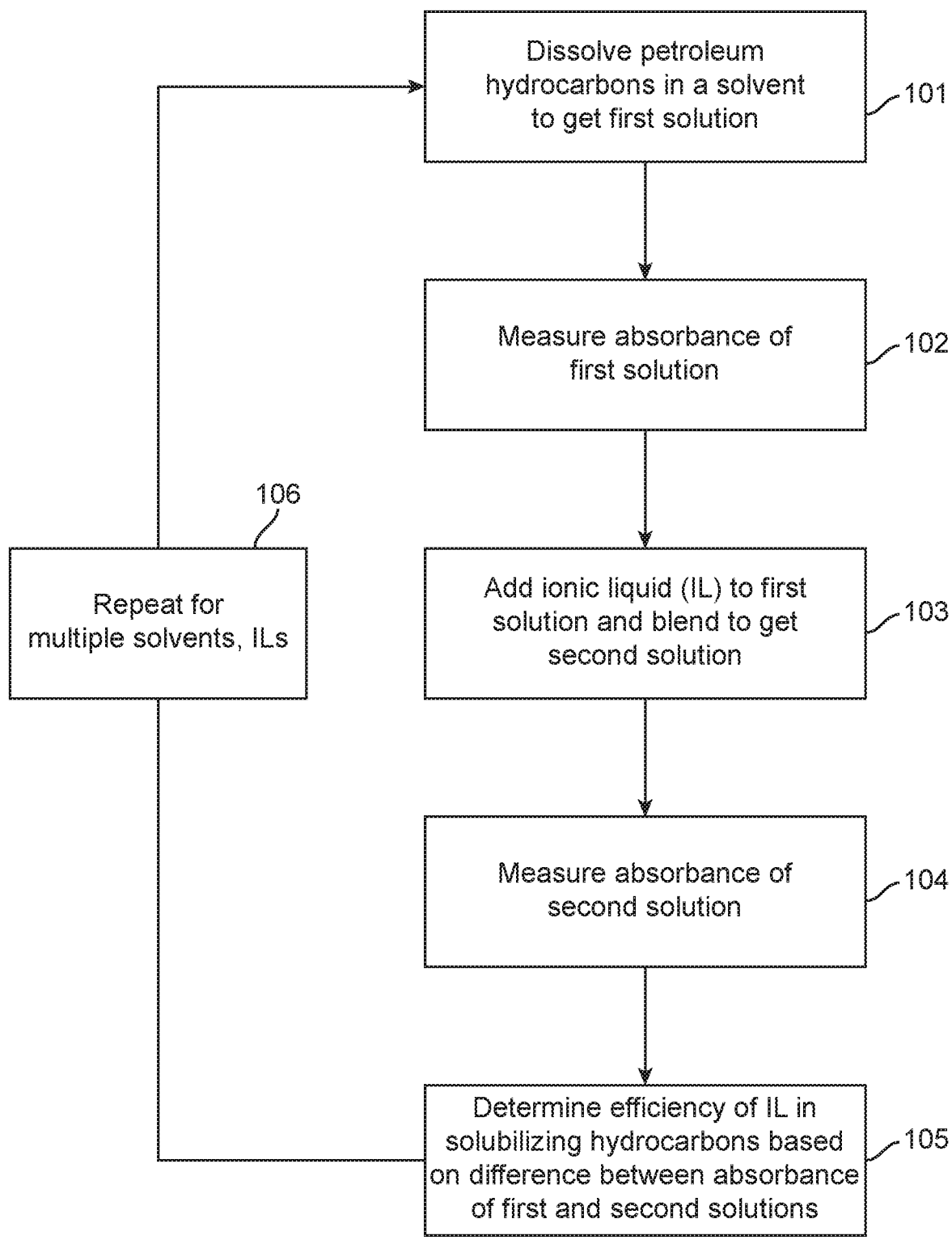
FIG. 1 illustrates one embodiment of a method of screening solvents for the solubilization of petroleum hydrocarbons.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

In one embodiment, the present disclosure is directed to a method for screening solubility of petroleum hydrocarbons. The method comprises selecting an aromatic or aliphatic solvent and dissolving petroleum hydrocarbons in the selected solvent to form a first solution. Subsequently, an ionic liquid (IL) is added to the first solution and mixed to form a second solution. The absorbance of the first and second solution is measured using a spectroscopic technique such as ultraviolet-visible (UV-Vis) spectrophotometry, Fourier transform-infrared spectroscopy (FT-IR) or $^{13}C$-nuclear magnetic resonance (NMR) spectroscopy. The measured absorbance is indicative of the solubility of petroleum hydrocarbons in the selected combination of solvent and IL.

One exemplary method of screening solvents for solubilization of petroleum hydrocarbons is illustrated in the flow chart shown in FIG. 1. At step 101, petroleum hydrocarbons are dissolved in a selected first solvent, and blended uniformly to form a first solution. At step 102, the absorbance of the first solution is measured using spectrometric techniques. At step 103, an IL is added to the first solution and blended to form a second solution. The absorbance of the second solution is measured using spectroscopic techniques in step 104. The measured absorbance value of the second solution is indicative of the concentration of the petroleum hydrocarbons in the selected solvent-IL combination. In step 105, the efficiency of the IL in solubilizing hydrocarbons is determined based on the difference in measured absorption of the first and second solutions. The solubilization of petroleum hydrocarbons in combinations of various solvents and ILs is then determined in step 106 by repeating steps 101 to 105 as shown in FIG. 1.

In one embodiment, the solvent is selected from a group of solvents including, but not limited to, aromatic hydrocarbon solvents, aliphatic hydrocarbon solvents, or mixtures thereof. In one embodiment, the aromatic hydrocarbon solvents may comprise benzene, ethyl benzene, xylene, phenol, toluene, and mixtures thereof; and the aliphatic hydrocarbon solvents may comprise pentane, hexane, heptane, octane, decane, ethyl acetate or mixtures thereof.

In one embodiment, the IL is chosen from a group of co-solvents including, but not limited to, 1,3-dimethylimidazolium 1,1,1-trifluoro-N-[(trifluoromethyl)-sulfonyl] methanesulfonamide; 1-butyl-1-methylpyrrolidinium 1,1,1-trifluoro-N-[(trifluoromethyl)sulfonyl]methanesulfonamide; diethylammonium phosphate; diethylammonium sulfate; triethylammonium phosphate; triethylammonium sulfate; tripropylammoniumsulfate; tributylammoniumsulfate; 1-butyl-3-methylimidazolium 1,1,1-trifluoro-N-[(trifluoromethyl)sulfonyl]methanesulfonamide; 1-butyl-3-methyl imidazolium chloride; 1-butyl-3-methyl imidazoliumhexafluorophosphate; 1-ethyl-3-methylimidazolium ethyl sulfate; 1-hexyl-3-methylimidazolium hexafluorophosphate; 1-decyl-3-methylimidazolium bis(trifluoromethylsulfonyl) imide; 1-octyl-3-methylimidazolium chloride; 1-hexyl-3-methylimidazolium hydrogen sulfate; triethylammoniumtetrafluoroborate; triethylammonium acetate; or mixtures thereof. However, the application of this method is not limited to these solvents alone but can be extended in a similar way for other solvents and co-solvents.

In one embodiment, the present disclosure is directed to a system 200 for screening solubility of petroleum hydrocarbons in a variety of solvents. The system 200 comprises a source of petroleum hydrocarbons 201, a solvent source 202, and a source of IL 203. The system 200 also comprises a mixing device 204 equipped with a blending means 204A for blending of petroleum hydrocarbons, the solvent and the IL to form a solvent mixture, a sensor 205 for detecting the absorbance of the solvent mixture in the spectral region and a control module 206 such as a computing device comprising at least one processor and one memory for determining the solubilization of petroleum hydrocarbons in the solvent using the absorbance values. In some aspects, the sensor could be a spectrometer, for example.

Figure 3:
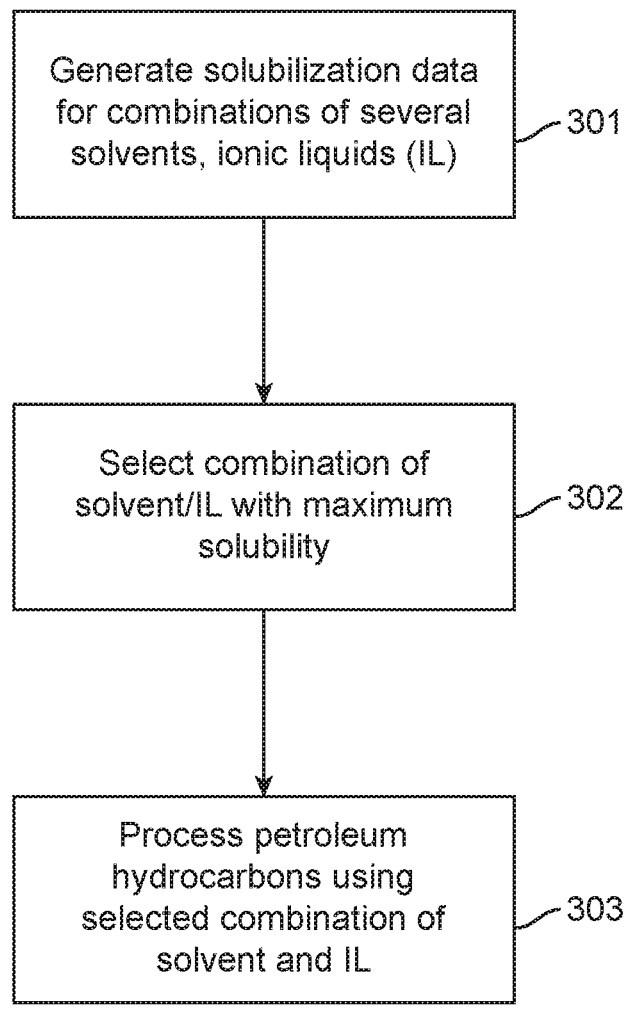
FIG. 3 illustrates another embodiment of a method of screening plurality of solvents for the solubilization of petroleum hydrocarbons.
Figure 4A:
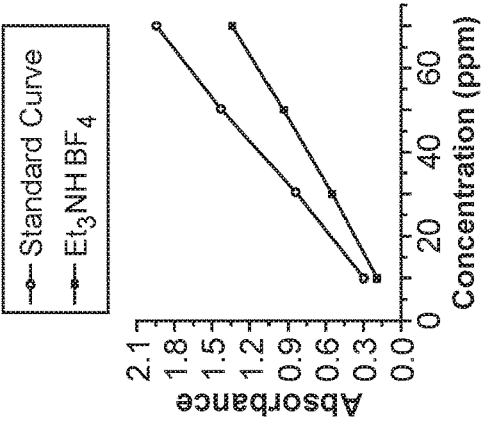
FIG. 4A-4H illustrates UV absorption showing the effect of 4A) $[Et_2NH_2]^+[H_2PO_4]^-$, 4B) $[Et_2NH_2]^+[HSO_4]^-$, 4C) $[Et_3NH]^+[CH_3COO]^-$, 4D) $[Et_3NH]^+[BF_4]^-$, 4E) $[Et_3NH]^+[H_2PO_4]^-$, 4F) $[Et_3NH]^+[HSO_4]^-$, 4G) $[Pr_3NH]^+[HSO_4]^-$ and 4H) $[Bu_3NH]^+[HSO_4]^-$ on HCO in heptane (HCO/ILs=1:1).
Figure 4B:
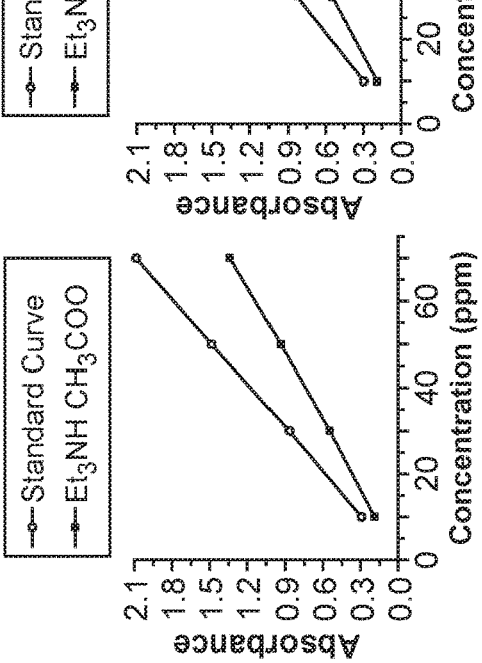
Figure 4C:
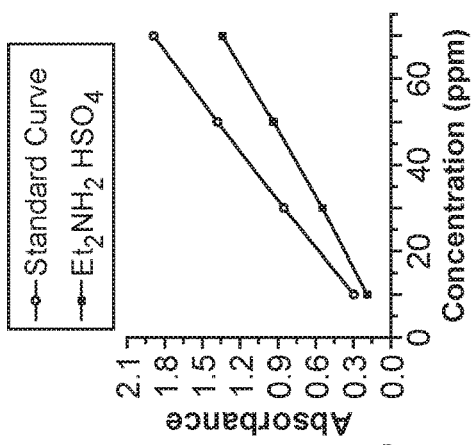
Figure 4D:
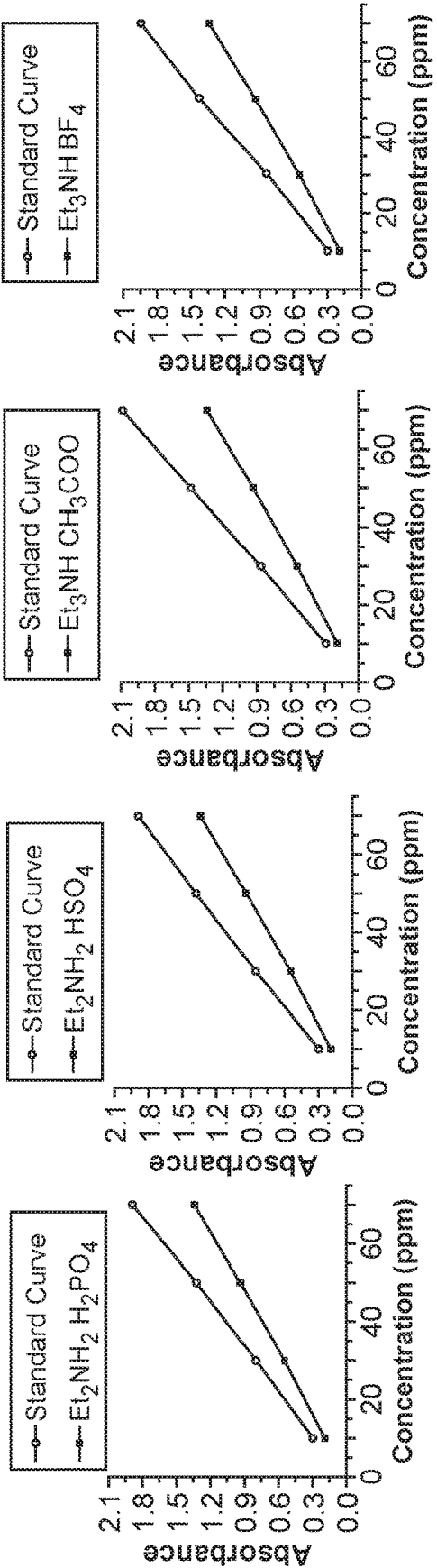
Figure 4E:
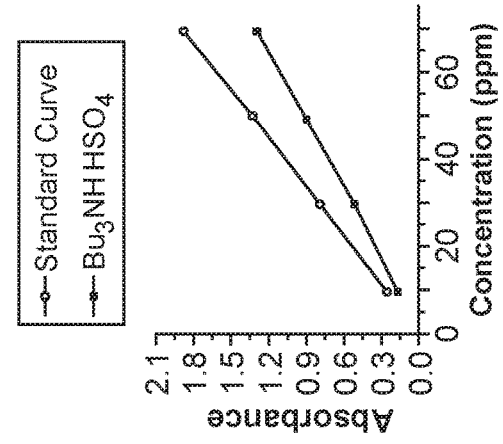
Figure 4F:
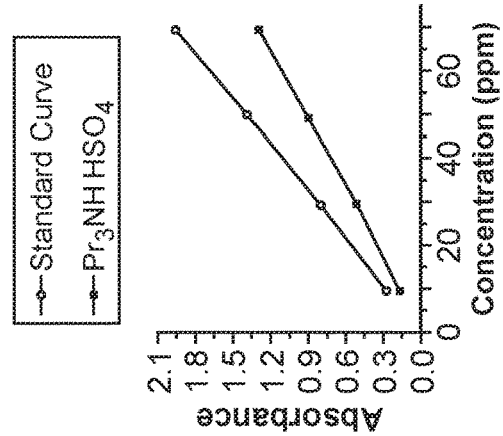
Figure 4G:
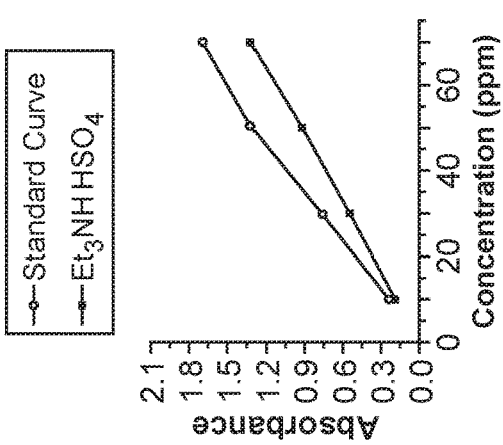
Figure 4H:
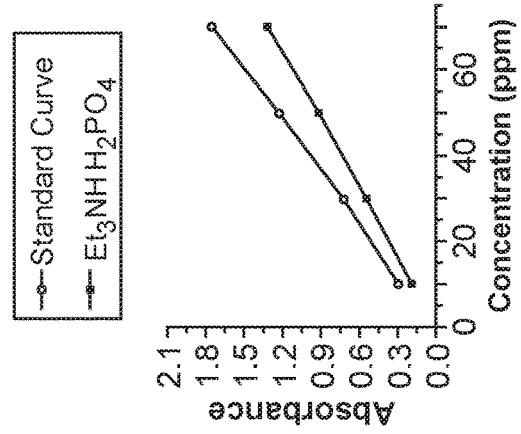

In another embodiment, the present disclosure is related to a method of processing petroleum hydrocarbons as described in FIG. 3. In step 301, the solubilization data of petroleum hydrocarbons in various combinations of solvent and ILs is generated based on the difference between the absorbance values of the first and second solutions as shown in FIG. 1. The absorbance value of the mixture of petroleum hydrocarbons in the second solution is usually higher than that of the first solution, thus revealing greater dissolution of petroleum hydrocarbons in the presence of the co-solvent (IL).

A combination of solvent and IL showing highest solubilization is selected in step 302, and the petroleum hydrocarbons are processed using the selected combination as in step 303. The absorbance values for different concentrations of petroleum hydrocarbons in selected solvents and ILs are measured. The absorbance for different concentrations increases due to the enhancement in the dissolution of the petroleum hydrocarbons in the solvent. In various embodiments shown in FIG. 1 to FIG. 3 the spectroscopic technique is one of ultraviolet-visible (UV-Vis) spectrophotometry, Fourier transform-infrared spectroscopy (FT-IR) or $^{13}C$-nuclear magnetic resonance (NMR) spectroscopy.

Figure 2:
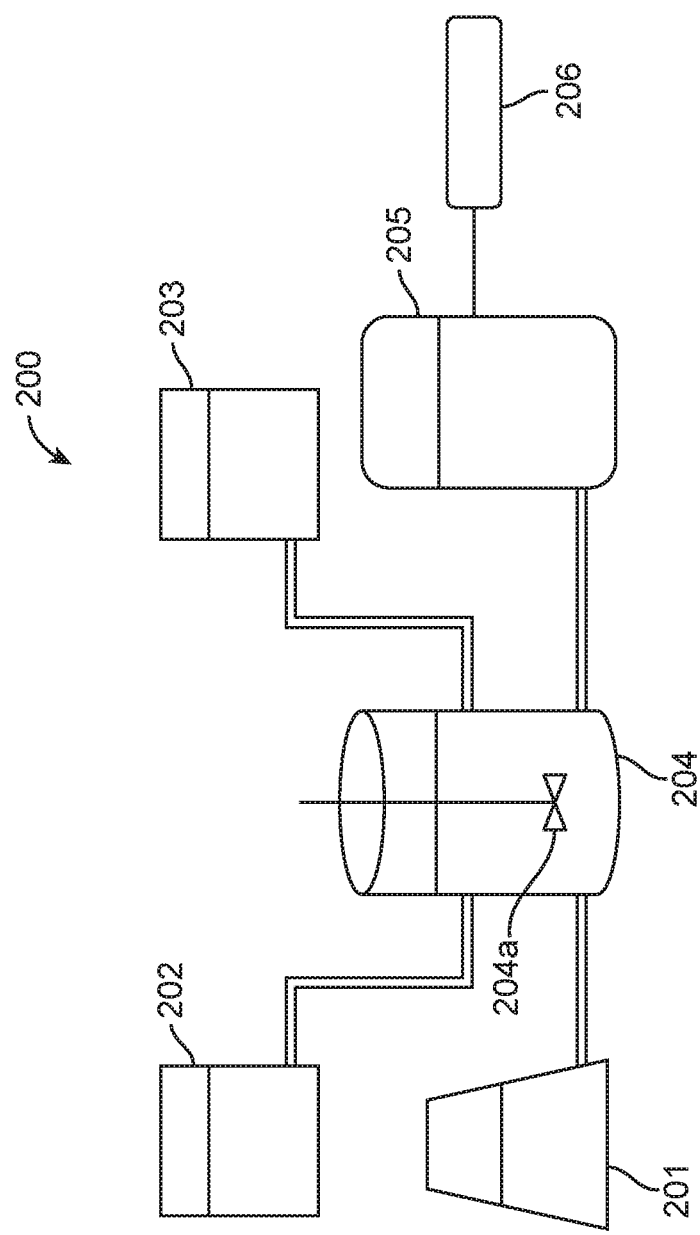
FIG. 2 illustrates one embodiment of a system of screening solvents for the solubilization of petroleum hydrocarbons.

As shown in FIG. 1 to FIG. 3, the use of the methods and systems disclosed herein enable rapid screening of solvent-co-solvent mixtures for solubilizing difficult to clean petroleum tank bottom sludge TBS. The methods and systems disclosed herein also enable rapid and efficient processing of petroleum tank sludge using a combination of solvent and co-solvent identified using the screening methods. The invention also discloses a system for rapid screening of solvents for solubilizing difficult to process solids.

The method and system disclosed are further elaborated with reference to the following examples.

Example 1

Heavy crude oil (HCO) samples were collected from Oil India Limited, Assam, India. HCO was more of a solid and was more viscous as compared to conventional crude oil. The SARA properties and other details of HCO are summarized in Table 1.

TABLE 1

SARA Analysis and API Gravity Report

| No. of trials | Composition | | | | API gravity |
|---|---|---|---|---|---|
| | Saturates (%) | Aromatics (%) | Resins (%) | Asphaltenes (%) | |
| 1 | 25.3 | 63.4 | 5.1 | 6.2 | 10.6 |
| 2 | 25.2 | 67.6 | 3.5 | 3.7 | 10.2 |
| 3 | 28.6 | 63.5 | 3.8 | 4.2 | 10.4 |
| Average | 26.4 | 64.8 | 4.1 | 4.7 | 10.4 |

Eight ILs, namely, $[Et_2NH_2]^+[H_2PO_4]^-$, $[Et_2NH_2]^+[HSO_4]^-$, $[Et_3NH]^+[CH_3COO]^-$, $[Et_3NH]^+[BF_4]^-$, $[Et_3NH]^+[H_2PO_4]^-$, $[Et_3NH]^+[HSO_4]^-$, $[Pr_3NH]^+[HSO_4]^-$, and $[Bu_3NH]^+[HSO_4]^-$ were synthesized and purified according to the methods available in the literature and were confirmed using $^1H$ nuclear magnetic resonance ($^1H$ NMR) spectroscopy. Preceding to their usage, all the ILs were dried under severe agitation at 353 K under vacuum (0.1 Pa) for a minimum of 48 h to remove volatile compounds and to reduce water content to negligible values.

Standard solutions containing HCO with solvents at different concentrations were prepared and their absorbance was recorded using UV-Vis spectrophotometer at fixed wavelength corresponding to the $\lambda_{max}$ Table 2. The $\lambda_{max}$ values were obtained by running full scan spectra of different concentrations of solution containing HCO in the specified solvent in the wavelength range of 190-900 nm.

TABLE 2

$\lambda_{max}$ of the HCO in Various Solvents

| Solvent | CAS no. | Source | Purity (%) | $\lambda_{max}$ (nm) |
|---|---|---|---|---|
| Decane | 124-18-5 | Aldrich | 95 | 227 |
| Ethyl acetate | 141-78-6 | Rankem | 99 | 257 |
| Heptane | 142-82-5 | Merck | 99 | 226 |
| Hexane | 110-54-3 | Merck | 99 | 229 |
| Toluene | 108-88-3 | Merck | 99 | 288 |

For studies relating to standard solution of HCO in toluene, the concentrations of solution used were: 10 ppm-100 ppm (with an increment of 10 ppm). For the rest of the solvents (heptane, decane, ethyl acetate, and hexane) the concentrations of the solutions (with respect HCO) used were in the range of 10 ppm to 120 ppm (with an increment of 10 ppm). The range with respect to toluene was kept to the minimum as much as possible to reduce the amount of solvent used as it is toxic, whereas the toxicity for the rest of the solvents was found to be comparatively lesser and, therefore, a wider range was considered.

Sample solution preparation for dissolution studies were carried out for varying ratios of HCO and ILs in the weight ratios of HCO/ILs as 1:1; 1:0.5, and 1:0.1. For HCO/ILs=1:

1, stock solution of 1000 ppm was prepared by dissolving 50 mg of heavy crude oil and 50 mg of IL in 50 mL of the corresponding solvent. For HCO/ILs=1:0.5 and 1:0.1, a similar procedure as described above was followed. The concentrations considered (i.e., 30, 50, 70 ppm for the case of toluene; 10, 30, 50, and 70 ppm for the rest) were made by dilution from the stock solution. The three different weight ratios of HCO to ILs were studied for all eight ionic liquids as mentioned above.

Further, for each ratio of HCO to ILs, four different concentrations (i.e., 10, 30, 50, 70 ppm) were prepared in four different solvents (i.e., heptane, decane, ethyl acetate, and hexane) and three different concentrations (i.e., 30, 50, 70 ppm) were prepared in toluene. Thus, a total of 456 sample solutions were prepared and each of them was prepared thrice from their respective stock solution, for three trial studies. The absorbance values for all of the sample solutions were recorded and were compared with their respective standard solution and were used for the calculation pertaining to the dissolution of heavy crude oil with solvent in the presence of ILs. The standard and sample solutions were freshly prepared and their absorbance was recorded on the same day approximately within 2 hours of solution preparation. For the hold-time study, the sample solutions were stored in a black chamber.

(a) Preparation of Sample for FT-IR and $^{13}$C NMR

Samples for FT-IR and $^{13}$C NMR analysis were prepared by decanting the dissolved portion of HCO with solvent (filtrate) from the sample prepared for UV-Vis spectra, followed by thoroughly washing the entire portion of the remaining residue to remove the ILs used. This portion of residue (obtained from the solutions containing 1:1 of HCO/ILs) was dried using a rotary evaporator, followed by oven-drying for 2 hours, both were maintained at 70° C. A small amount of the solid portion obtained was divided into two portions. One portion was used for recording $^{13}$C NMR, and the rest was used for recording the FT-IR spectra after being ground with potassium bromide (KBr). ILs used in the sample solution was recovered by the use of water which was recycled and can be reused. The same procedure was followed for all the five solvents. The amount of sample and KBr used was maintained uniform throughout the investigation.

(b) Solubility Studies of Heavy Crude Oil without ILs

The softening of the heavy crude oil by its dissolution in various solvents (standard solutions) was studied by measuring absorbance using the UV-vis spectrophotometer at the particular wavelength corresponding to the $\lambda_{max}$ of HCO in the respective solvent concerned (as shown in Table 2). The graphs of absorbance of standard solutions against the concentration (in ppm) of the heavy crude oil in solvents such as toluene, heptane, decane, ethyl acetate, and hexane, respectively were drawn. These concentrations (in ppm) versus absorbance graphs were fitted with linear regression analysis with a regression coefficient (R2) greater than 0.99. The equations and corresponding values of $R^2$ (correlation coefficient) obtained for various standard solutions of heavy crude oil in pure solvents (without ILs) are shown in Table. 3.

TABLE 3

Reference UV-Vis Absorbance of HCO in Various Solvents

| Solvent | Regression Equation | Correlation Coefft. |
|---|---|---|
| Toluene | y = 0.006x | 0.9980 |
| Heptane | y = 0.0195x | 0.9982 |

TABLE 3-continued

Reference UV-Vis Absorbance of HCO in Various Solvents

| Solvent | Regression Equation | Correlation Coefft. |
|---|---|---|
| Decane | y = 0.0219x | 0.9993 |
| Ethyl acetate | y = 0.0123x | 0.9997 |
| Hexane | y = 0.0237 | 0.9995 |

(c) Solubility Studies of Heavy Crude Oil with ILs

The solubility studies of the sample solutions with eight ILs, five solvents and with three different weight-ratios of HCO/ILs were done by measuring their absorbance at a particular wavelength corresponding to the $\lambda_{max}$ of HCO in the respective solvent concerned (as provided in Table 2). All the values corresponding to the absorbance runs were consistent for three trials and were fund to be within ±0.001 of the reported values. The absorbance of the sample solutions were compared with the respective concentration of the standard solutions and the increase in the percentage solubility over standard solution (with absorbance values of standard solution as the base reference) were calculated and plotted. FIGS. 4A-4H show the efficiency of eight ILs in the dissolution of heavy crude oil following the order, $[Et_2NH_2]^+[H_2PO_4]^-$, $[Et_2NH_2]^+[HSO_4]^-$, $[Et_3NH]^+[CH_3COO]^-$, $[Et_3NH]^+[BF_4]^-$, $[Et_3NH]^+[H_2PO_4]^-$, $[Et_3NH]^+[HSO_4]^-$, $[Pr_3NH]^+[HSO_4]^-$, and $[Bu_3NH]^+[HSO_4]^-$.

Figure 5:
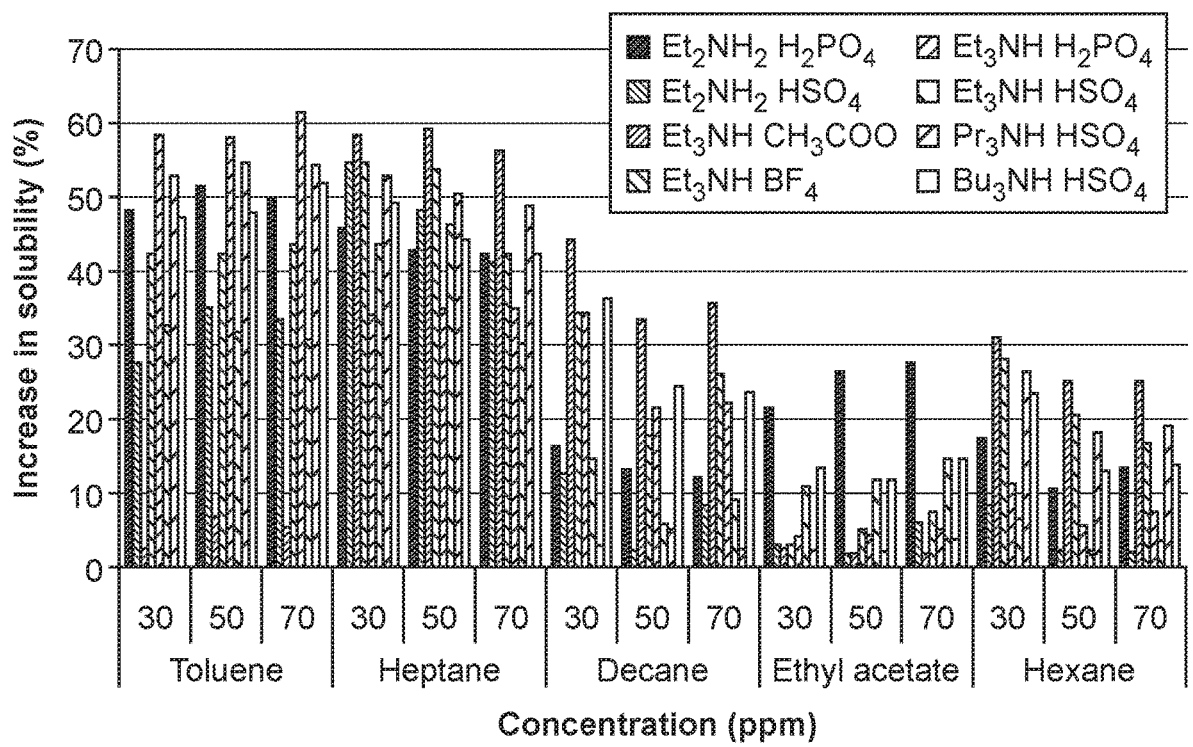
FIG. 5 shows the comparison of the efficiency of all the ILs in terms of increase in solubility of HCO in all of the mentioned solvents containing a varying ratio of 1:1 (HCO/ILs) at three different concentrations. Base line of 0% solubility is for the standard solution.

FIG. 5 shows the percentage increase in solubility (with an accuracy of ±0.1%) with an increase in the concentration of HCO in solvent (in ppm) for different weight ratios of HCO/ILs, showing the effectiveness of various ILs on the solubility of heavy crude oil.

With reference to the results shown in FIGS. 4 and 5, the dissolution of heavy crude oil in toluene was observed to be more efficient in the presence of $[Et_3NH]^+[H_2PO_4]^-$. Minimum efficiency of less than 10% was observed for the IL, $[Et_3NH]^+[CH_3COO]^-$. In the case of the solvent heptane, the IL $[Et_3NH]^+[CH_3COO]^-$ exhibited the maximum efficiency of about 70% for the dissolution of heavy crude oil while with other ILs showed an overall better performance of around 30%. For the case of the solvent decane, $[Et_3NH]^+[CH_3COO]^-$ showed an efficiency to the maximum of around 45% in the dissolution of heavy crude oil and for the concentration of 10 ppm of heavy crude oil in decane, the ILs, namely, $[Et_3NH]^+[H_2PO_4]^-$, $[Et_3NH]^+[BF_4]^-$, and $[Bu_3NH]^+[HSO_4]^-$, showed around 50% efficiency. In the case of ethyl acetate, the IL, $[Et_2NH_2]^+[H_2PO_4]^-$, provided an efficiency of up to 32% at 10 ppm concentration for a 1:1 ratio of HCO/IL for the dissolution of heavy crude oil and the ILs, such as $[Et_3NH]^+[HSO4]^-$ and $[Bu_3NH]^+[HSO_4]^-$, showed better performance next to $[Et_2NH_2]^+[H_2PO_4]^-$.

Other ILs showed <5% efficiency for the dissolution of heavy crude oil. In the case of hexane, $[Et_3NH]^+[CH_3COO]^-$ showed an efficiency of around 62% followed by $[Et_3NH]^+[BF_4]$ and $[Pr_3NH]^+[HSO_4]$ at 10 ppm concentration for a 1:1 ratio of HCO/IL. In addition, it was noted that the efficiency of dissolution of heavy crude oil decreased with increasing concentrations of heavy crude oil in hexane, for all three weight-ratios of HCO/ILs used. The best of ILs based on their effectiveness to solubilize heavy crude oil in the presence of various solvents (on the basis of 30 ppm concentration, in the ratio of HCO/IL=1:1) are shown in Table 4. In some aspects, these ranking may slightly vary with changes in concentration of heavy crude oil in solvent but essentially would follow similar trends.

TABLE 4

Best of ILs based on their efficiency in the enhancement of dissolution of HCO in five solvents, with respect to 30 ppm concentration of heavy crude oil in the respective solvent (HCO/IL = 1:1)

| Solvents | Name of IL | Chemical Formula | Solubility Increase (%) |
|---|---|---|---|
| Toluene | Triethylammonium phosphate | $[Et_3NH]^+[H_2PO_4]^-$ | 58.60 |
| Heptane | Triethylammonium acetate | $[Et_3NH]^+[CH_3COO]^-$ | 58.61 |
| Decane | Triethylammonium acetate | $[Et_3NH]^+[CH_3COO]^-$ | 44.55 |
| Ethyl acetate | Diethylammonium phosphate | $[Et_2NH2]^+[H_2PO_4]^-$ | 21.91 |
| Hexane | Triethylammonium acetate | $[Et_3NH]^+[CH_3COO]^-$ | 31.19 |

Figure 6:
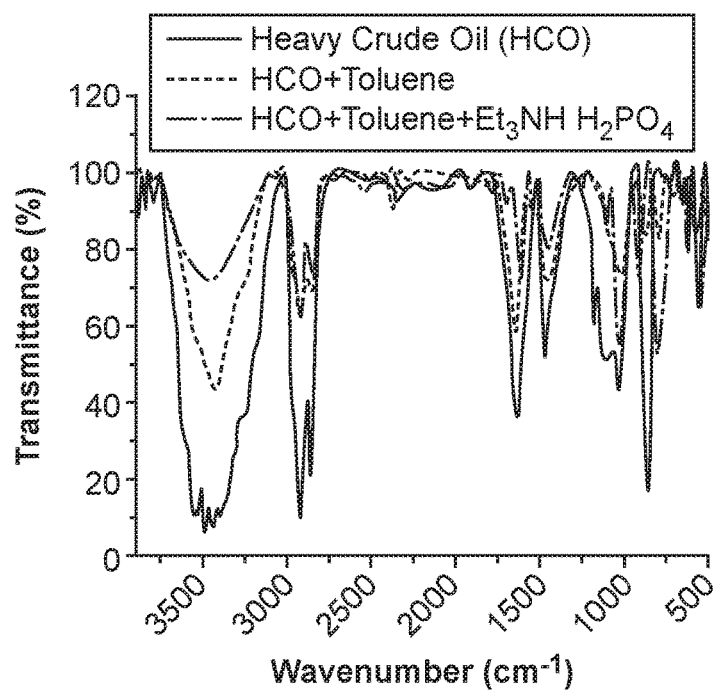
FIG. 6 shows FT-IR spectra of crude HCO, HCO+Toluene, and HCO+Toluene+$[Et_3NH]^+[H_2PO_4]^-$.

In general, with respect to the different weight-ratios of HCO/ILs, only 10% of IL was found to be sufficient to cause efficient dissolution of heavy crude oil in various solvents. From FIG. 6, showing the comparison of solvents in the presence of ILs, it was concluded that the performance of toluene and heptane showed the highest efficiency in softening and dissolution of heavy crude oil in the said solvents whereas poor performance was observed for ethyl acetate and hexane.

In comparing the efficiencies of similar solvents, namely, hexane and heptane, heptane was observed to perform better than hexane. In some aspects, the reason was attributed to the tendency of hexane to sequester to some extent, depending on its ability, the components of crude oil (aromatics/resins/asphaltenes) which were principally UV active. The remaining free groups, i.e., saturates (UV inactive) along with a meager amount of the UV active components were then available to take part in further processes, which resulted in very low absorbance values indicating less solubility of HCO with hexane. In that case, hexane was presumed to possess greater sequestration tendency as compared to heptane.

(d) Hold-Time Study

Hold-time study was carried out for a sample case for the dissolution of heavy crude oil in heptane as solvent with and without ILs using the UV-Vis spectrophotometric technique. The study showed that on holding in the solvent for up to 30 days, the increase in the dissolution of the heavy crude oil was observed to be in the range of 11-16% for the standard solution (heavy crude oil in heptane without ILs) and 61-222% for the sample solutions (heavy crude oil in heptane with various ILs). On comparing the solution of HCO+heptane and the solution of HCO+heptane+IL, when the latter was stored for a prolonged period, the ILs acquired more chance of interaction with HCO, that paved the way for extra softening of the HCO.

(e) FT-IR Spectral Analysis

FT-IR spectral analysis was determined for the crude HCO, the treated HCO with neat solvents alone, and with solvent+ILs. The FT-IR spectra for the three cases using toluene are shown in FIG. 6. The results were in good agreement with the results of UV-Vis studies.

For the FT-IR analysis of heavy crude oil with solvents, the ILs used were the ones giving a higher percentage of dissolution of HCO with an accuracy of ±0.1% based on UV-Vis studies. For the virgin HCO and the treated HCO with solvent and with solvent+ILs, mineral bands (predominantly clay and sands) around 1100, 800, and 500 cm$^{-1}$ exhibited strong absorption in the infrared region. The absorption modes observed around 1450 cm$^{-1}$ corresponded to the C—H bending frequency, peak at 2950 cm$^{-1}$ corresponded to C—H stretching frequency, and the peak around 3500 cm$^{-1}$ corresponded to OH/H$_2$O.

The highest absorbance was noted between 2900 and 3000 cm$^{-1}$ showing the presence of methylene groups, (e.g., alkanes) of the heavy crude oil. For the treated heavy crude oil with different solvents such as toluene, heptane, decane, ethyl acetate, and hexane, a significant drop in the intensity of the peaks were observed. The decrement in the intensity of the peaks showed that the proportion of HCO had decreased considerably and was evidently more convincing in the case of the HCO treated with solvent and IL together than HCO with the neat solvent alone. In the spectrum of the HCO, intense bands were seen as a sharp doublet near 1010 cm$^{-1}$ which were due to kaolinite (a clay mineral), and these modes were superimposed on absorbance due to other clays. A doublet near 800 cm$^{-1}$ corresponded to silicates.

(f) NMR Spectral Analysis

Figure 7A:
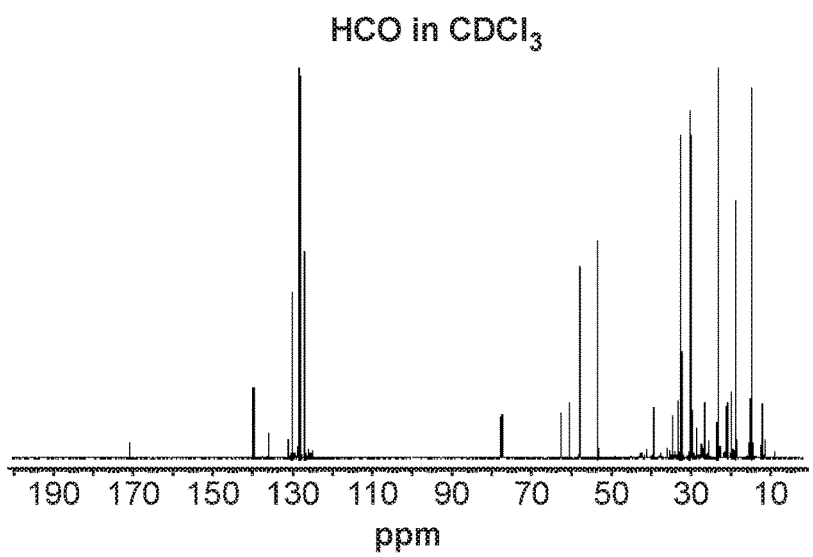
FIGS. 7A-7C illustrates the $^{13}C$ NMR spectra of 7A) HCO, 7B) heptane treated HCO and 7C) HCO treated with heptane along with $[Et_3NH]^+[CH_3COO]^-$.
Figure 7B:
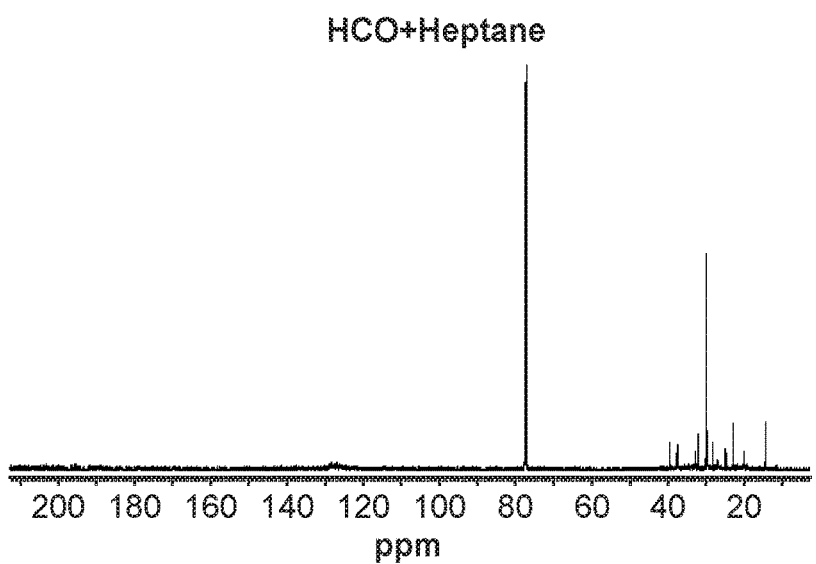
Figure 7C:
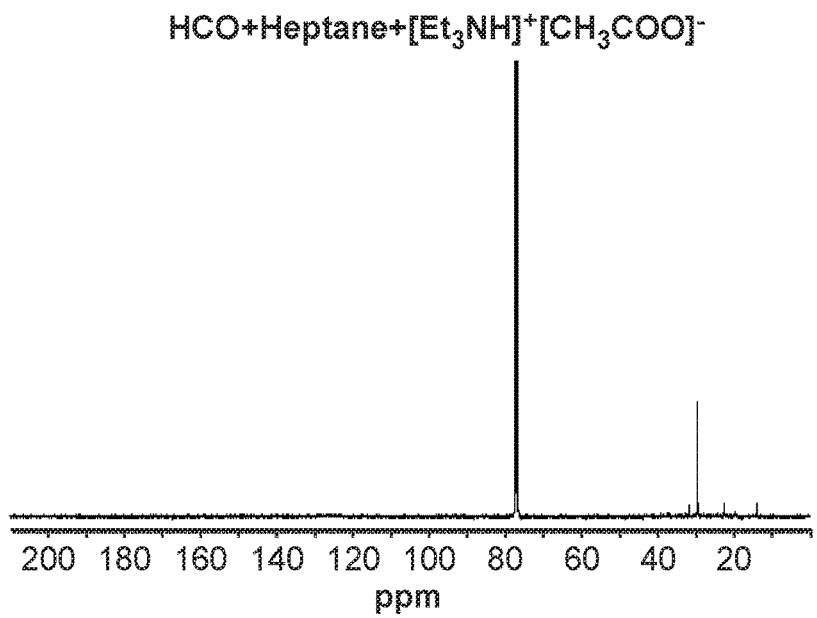

FIGS. 7A-7C present the $^{13}$C NMR spectra of the HCO, the treated bottom sediments of the heavy crude oil with neat solvent, and HCO in solvent with ILs, respectively. The IL $[Et_3NH]^+[CH_3COO]^-$ was considered for analysis of HCO in heptane, based on its better performance in solubility as observed in UV-Vis and FT-IR studies as discussed earlier. It was observed that, in the case of HCO, there were several peaks in the region between 10 and 55 ppm, which predicted the presence of aliphatic methyl and methylene carbon atoms in HCO. These peaks got weakened in the case of heptane treated HCO and nearly vanished in the spectrum for the IL treated HCO in heptane. Like the FT-IR results, these $^{13}$C NMR results were also consistent with the earlier discussed results indicating enhanced solubility of crude oil in the solvent and ionic liquid system.

In FIG. 7A, a peak around 170 ppm was observed for the crude HCO, which was an indication of the >C═O group present in the HCO. The peaks visible in the region of 120-140 ppm indicated the presence of aromatics in the HCO. It was observed from FIG. 7B that these peaks do not vanish completely, indicating that there was oil still present in the sample. In FIG. 7C, the peaks due to the aromatics disappeared, signifying the absence of oil after the treatment of heavy crude oil in heptane with the IL, $[Et_3NH]^+[CH_3COO]^-$.

In general, from the present investigation, it was observed that the presence of ILs along with solvents enhanced the dissolution of HCO making them easily pumpable and transportable through pipelines. The hold-time study also provided reliable information for the use of appropriate ILs and solvents for efficient softening of the HCO thereby preventing sludge deposition in storage tanks, in transportation pipelines, and in the reservoirs.

10% of IL for almost complete dissolution of HCO in organic solvent was adequate. $[Et_3NH]^+[H_2PO_4]^-$ exhibited good performance in the dissolution of HCO in toluene, whereas in the case of heptane, decane, and hexane $[Et_3NH]^+[CH_3COO]^-$ showed better performance and in ethyl acetate $[Et_2NH_2]^+[H_2PO_4]^-$ gave better results. Comparing the efficiency of solvents with respect to their enhancement in dissolution of HCO followed the order as toluene>heptane>decane>ethyl acetate>hexane.

The results of FT-IR and $^{13}$C NMR also supported the results obtained using UV-vis studies. The hold-time study revealed that the contact of HCO with heptane alone for a prolonged period (30 days) dissolved about 16% of HCO, while in case of heptane+IL ([Et$_3$NH]$^+$[CH$_3$COO]$^-$) it was increased by about 222%. Thus the minimal usage of ILs (green solvents) is sufficient for dissolution of HCO, and its exploitation in large scale for petroleum industries would provide room for environmentally friendly atmosphere.

Example 2

Standard solutions were prepared from stock solution of tank bottom sludge (TBS) collected from Oil India Limited, Assam, India. The solvents viz., heptane and toluene were considered for the experiments and absorbance values for all the solutions (TBS+solvents) were recorded and were compared with the absorbance of the standard solution and further calculations were performed as illustrated in Example 1.

Figure 8A:
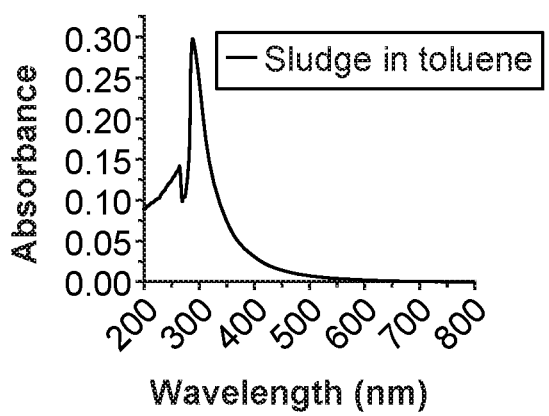
FIGS. 8A and 8B show UV-Vis spectra of standard solution of TBS in toluene and heptane, respectively.
Figure 8B:
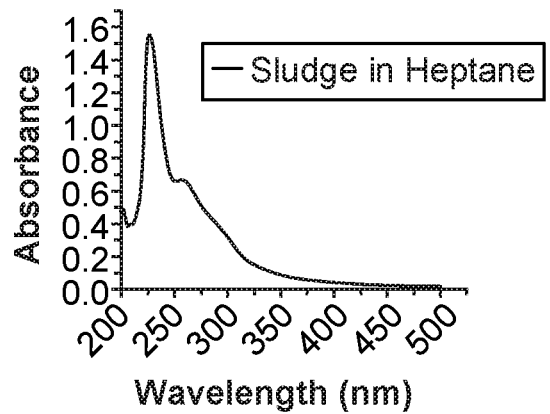

(a) IR Spectra for TBS and Calibration of the Standard Solutions Containing the TBS in Solvent:

IR spectra of the TBS sample was obtained using FT-IR spectrophotometer, which showed the C—H stretching and C—H bending frequencies corresponding to the crude oil present in the TBS. Peak at 1457 cm$^{-1}$ corresponding to C—H bending frequency, peak at 2920 cm$^{-1}$ corresponding to C—H stretching frequency and the peak at 3418 cm$^{-1}$ corresponding to O—H/H$_2$O were observed. The full scan UV-Vis spectra of the 'TBS+toluene' and 'TBS+heptane' standard solutions are shown in FIGS. 8A and 8B respectively. These results were used to compare the UV-Vis spectra of TBS in solvent with ionic liquids and also for determining the $\lambda_{max}$ as illustrated in Table 2.

The standard calibration curve was obtained for the different concentrations of TBS in toluene ranging from 10 ppm-100 ppm. The absorbance values were recorded by fixing the wavelength to the corresponding $\lambda_{max}$ of TBS in toluene (i.e. $\lambda_{max}$=288 nm) (Table 2). The data was fitted to a linear plot with a regression value R$^2$=0.99796. The standard calibration curve was obtained for the TBS in heptane at different concentrations ranging from 10 ppm-120 ppm. The absorbance values were recorded by fixing the wavelength to the corresponding $\lambda_{max}$ of TBS in heptane. The data was fitted to a linear plot with a regression value R$^2$=0.99554. The linear fit equations for toluene and heptane are y=0.006x and y=0.0195x, respectively.

(b) Effect of ILs on the Solutions Containing the TBS in Toluene:

Seven ILS, namely 1-butyl-3-methyl imidazolium chloride [BMIM]$^+$[Cl]$^-$, 1-butyl-3-methyl imidazoliumhexafluorophosphate [BMIN]$^+$[PF6]$^-$, diethylammonium phosphate [Et$_2$NH$_2$]$^+$[H$_2$PO$_4$]$^-$, 1-octyl-3-methylimidazolium chloride [OMIM]$^+$[Cl]$^-$, 1-hexyl-3-methylimidazolium hydrogen sulfate [HMIM]$^+$[HSO4]$^-$, triethylammoniumtetrafluoroborate [Et$_3$NH]$^+$[BF$_4$]$^-$, triethylammonium acetate [Et$_3$NH]$^+$[CH$_3$COO]$^-$, were chosen for this study.

Figure 9:
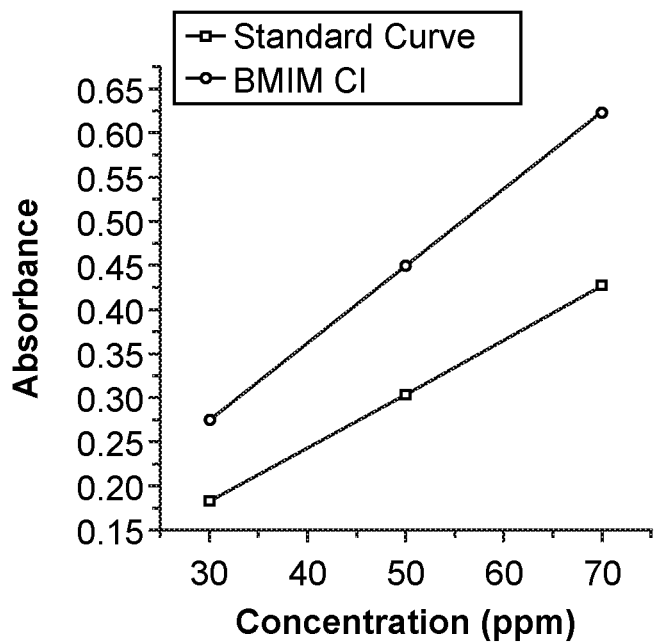
FIG. 9 shows the effect of ionic liquid (BMIM Cl) on absorbance with different concentrations of TBS in toluene.

The absorbance for the samples, i.e. the solution containing TBS, toluene and ionic liquids, at 3 different concentrations of TBS in toluene at 30 ppm, 50 ppm, 70 ppm in solvent+ionic liquid, was determined in the same way by fixing the wavelength at the corresponding max of the TBS in toluene (i.e. at $\lambda_{max}$=288 nm; see Table 2). The effect of [BMIM]$^+$[Cl]$^-$ addition to TBS in toluene is shown as example in FIG. 9, depicting the comparison of absorbance of the standard solution (TBS in toluene) with the effect of addition of ILs to the standard solution. Table 5 gives the numerical data for all seven ILs, showing the effect of IL addition through increase in the absorbance values.

The absorbance values in Table 5 correspond to the concentration of the TBS in the solvent. As a result of addition of the various ILs, the absorbance for different concentrations of the sample increases due to the enhancement in the dissolution of the TBS in the solvent. The concentration (ppm) refers strictly to the concentration of the TBS in the solvent only and not of the IL as the latter do not give any absorbance in UV-spectra.

Figure 10:
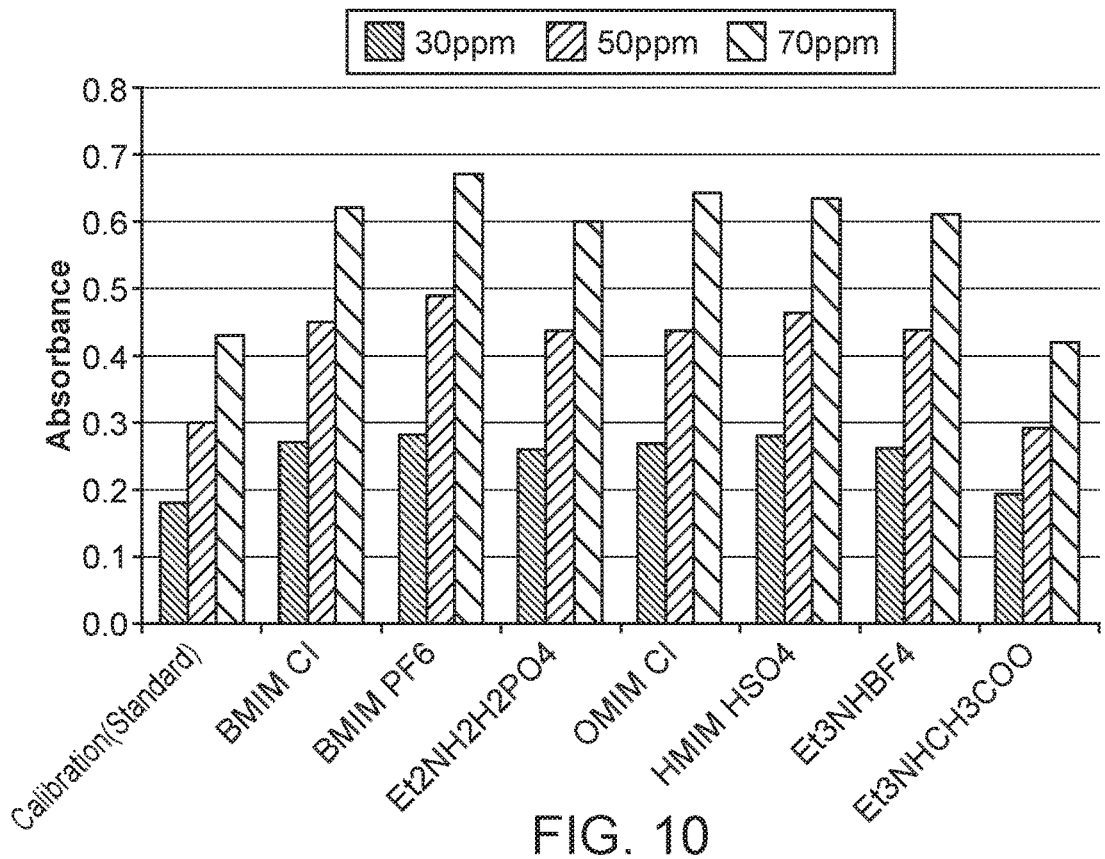
FIG. 10 is a bar chart showing change in absorbance values containing TBS at three different concentrations in toluene for various ionic liquids.

The effect of addition of ILs to the standard solution (TBS in toluene) is illustrated in FIG. 10. This bar diagram depicts the increase in the absorbance values in comparison with the standard. From FIG. 10, it is evident that among the ILs under study [BMIN]$^+$[PF$_6$]$^-$ is more efficient to increase the concentration of the TBS in the solution, followed by the other co-solvents. The evidence to support this trend is given in Table 6 showing the numerical data for the percentage increase in the solubility of the TBS in toluene.

TABLE 5

Comparison of absorbance of different ILs and TBS in toluene with the standard (TBS in toluene)

| S. No. | Co-solvent (IL) Concentration of TBS in toluene | Absorbance | | |
|---|---|---|---|---|
| | | 30 ppm | 50 ppm | 70 ppm |
| | Without cosolvent in toluene | 0.18 | 0.30 | 0.43 |
| 1 | BMIM Cl | 0.27 | 0.45 | 0.62 |
| 2 | BMIM PF$_6$ | 0.28 | 0.49 | 0.67 |
| 3 | Et$_2$NH$_2$H$_2$PO$_4$ | 0.26 | 0.44 | 0.60 |
| 4 | OMIM Cl | 0.27 | 0.44 | 0.64 |
| 5 | HMIM HSO$_4$ | 0.28 | 0.46 | 0.63 |
| 6 | Et$_3$NHBF$_4$ | 0.26 | 0.44 | 0.61 |
| 7 | Et$_3$NHCH$_3$COO | 0.19 | 0.29 | 0.42 |

TABLE 6

Increase in the solubility of TBS in toluene with the use of various ionic liquids

| S. No | Co-solvent (IL) Initial concentration of TBS in toluene | Increase in the solubility (%) of TBS in toluene after addition of various ionic liquids (TBS:ILs = 1:1) | | |
|---|---|---|---|---|
| | | 30 ppm | 50 ppm | 70 ppm |
| 1 | BMIM Cl | 52.37 | 48.17 | 46.09 |
| 2 | BMIM PF$_6$ | 57.43 | 60.32 | 56.99 |
| 3 | Et$_2$NH$_2$H$_2$PO$_4$ | 42.31 | 46.47 | 39.54 |
| 4 | OMIM Cl | 45.05 | 45.64 | 50.33 |
| 5 | HMIM HSO$_4$ | 53.34 | 50.46 | 46.50 |
| 6 | Et$_3$NHBF$_4$ | 45.05 | 44.84 | 43.87 |
| 7 | Et$_3$NHCH$_3$COO | 4.04 | −3.84 | −2.67 |

Figure 11:
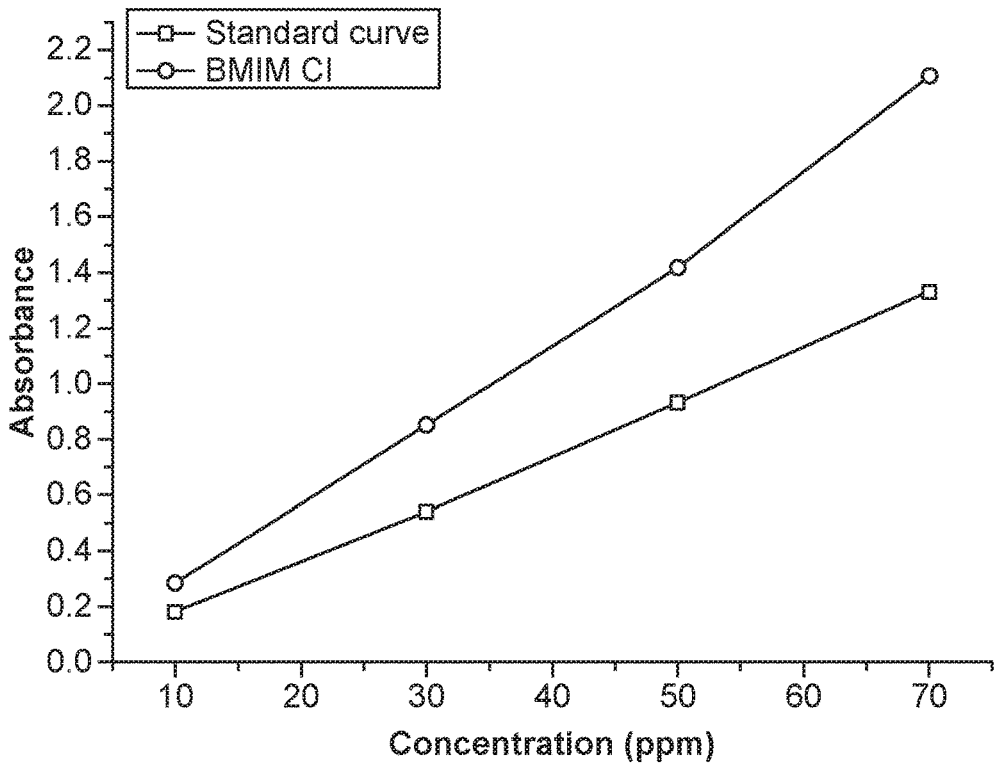
FIG. 11 shows the effect of ionic liquid (BMIM Cl) on absorbance with different concentrations of TBS in heptane.

(c) Effect of ILs on the Solutions Containing the TBS in the Solvent Heptane:

The absorbance for the samples i.e., the solution containing TBS, heptane and ionic liquids, at 4 different concentrations of TBS in heptane 10 ppm, 30 ppm. 50 ppm, 70 ppm in solvent+ionic liquid was determined in the same way by fixing the wavelength at the corresponding $\lambda_{max}$ of the TBS in heptane (i.e.; at $\lambda_{max}$=226 nm; see Table 2). The effect of [BMIM]$^+$[Cl]$^-$ addition to TBS in heptane is shown as example in FIG. 11, depicting the comparison of absorbance of the standard solution (TBS in heptane) with the effect of addition of ILs to the standard solution. Table 7 gives the numerical data showing the effect of addition of IL to the standard (TBS in heptane) by means of the increase in the absorbance values for all 7 ILs studied.

Figure 12:
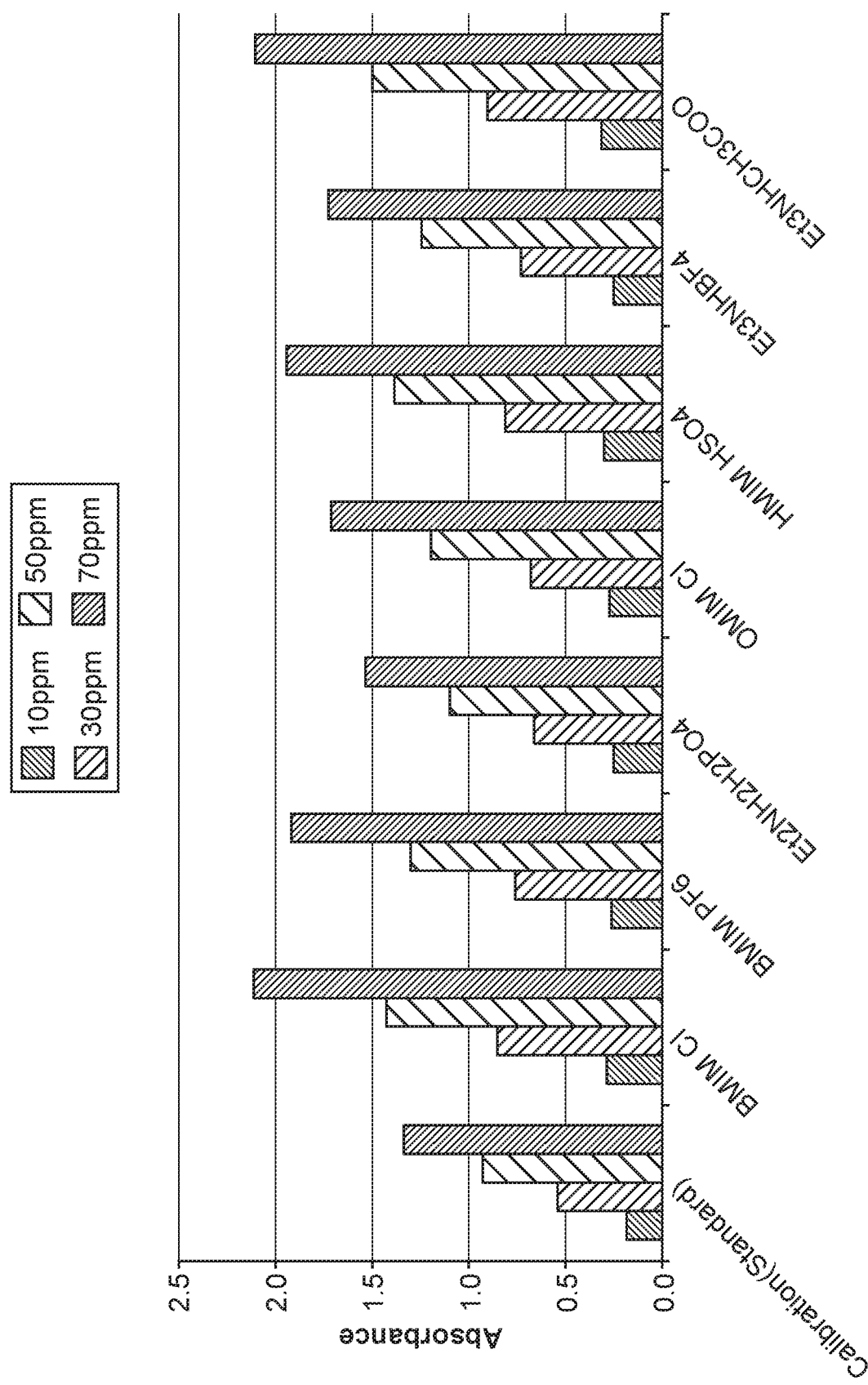
FIG. 12 is a bar chart showing the absorbance values of a solution containing TBS in heptane and various ionic liquids.

The effect of addition of all seven ILs to the standard solution is illustrated in FIG. 12. This bar diagram clearly depicts the increase in the absorbance of the solutions containing TBS in heptane+IL in comparison with the standard solution for four levels of TBS concentration in the solvent. The corresponding numerical data is given in Table 8 showing the increase in the solubility of TBS in heptane in terms of percentage. The absorbance values (in Table 7) correspond to the concentration of the TBS in the solvent. As a result of addition of the various ILs, the absorbance for different concentrations of the sample increases due to the enhancement in the dissolution of the TBS in the solvent.

TABLE 7

Comparison of absorbance of solutions containing different ILs and TBS in heptane with the standard (TBS in heptane)

| S. No | Co-solvent (IL) Concentration of TBS in heptane | Absorbance | | | |
|---|---|---|---|---|---|
| | | 10 ppm | 30 ppm | 50 ppm | 70 ppm |
| | Without cosolvent in heptane | 0.18 | 0.54 | 0.93 | 1.33 |
| 1 | BMIM Cl | 0.28 | 0.85 | 1.42 | 2.11 |
| 2 | BMIM $PF_6$ | 0.26 | 0.76 | 1.30 | 1.91 |
| 3 | $Et_2NH_2H_2PO_4$ | 0.25 | 0.66 | 1.10 | 1.53 |
| 4 | OMIM Cl | 0.27 | 0.68 | 1.19 | 1.71 |
| 5 | HMIM $HSO_4$ | 0.30 | 0.81 | 1.37 | 1.93 |
| 6 | $Et_3NHBF_4$ | 0.25 | 0.73 | 1.24 | 1.72 |
| 7 | $Et_3NHCH_3COO$ | 0.31 | 0.90 | 1.50 | 2.09 |

TABLE 8

Increase in the solubility of TBS in heptane with the use of various ILs

| S.No | Co-solvent (IL) Initial concentration of TBS in heptane | Increase in the solubility (%) of TBS in heptane after addition of various ionic liquids (TBS:ILs = 1:1) | | | |
|---|---|---|---|---|---|
| | | 10 ppm | 30 ppm | 50 ppm | 70 ppm |
| 1 | BMIM Cl | 54.82 | 56.52 | 52.56 | 58.51 |
| 2 | BMIM $PF_6$ | 41.67 | 40.86 | 40.04 | 44.04 |
| 3 | $Et_2NH_2H_2PO_4$ | 35.19 | 22.04 | 18.40 | 15.11 |
| 4 | OMIM Cl | 49.21 | 25.85 | 28.08 | 28.92 |
| 5 | HMIM $HSO_4$ | 65.24 | 48.65 | 47.55 | 45.44 |
| 6 | $Et_3NHBF_4$ | 38.96 | 34.10 | 33.71 | 29.29 |
| 7 | $Et_3NHCH_3COO$ | 68.14 | 65.66 | 61.81 | 57.21 |

Figure 13:
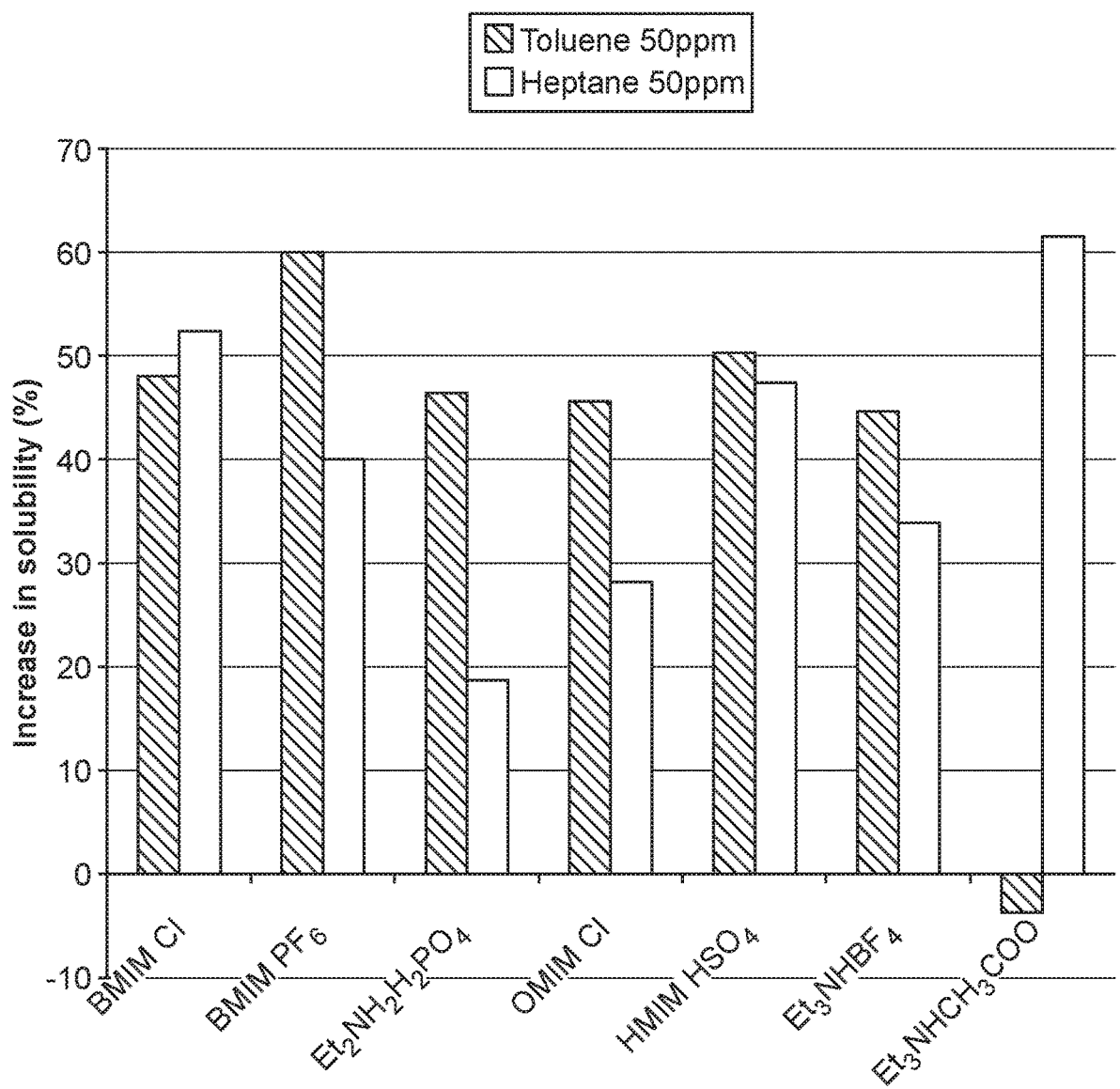
FIG. 13 is a comparison chart representing the efficacy of various ionic liquids under study in standard solutions containing 50 ppm of TBS in toluene and heptane.

(d) Comparison of the Efficacy of the ILs with the Solutions Containing the TBS in Toluene and Heptane The effectiveness of the addition of ILs to the solutions containing the TBS in toluene in comparison with the solution of TBS in heptane is shown in FIG. 13 as an example, for 50 ppm concentration of TBS in the solvents in terms of UV absorbance. This bar diagram clearly depicts the percentage increase in the solubility of the TBS in the solvent with the addition of ILs.

(e) Day-Hold Study for the TBS in Heptane (Standard Solution)

Standard solution (TBS in heptane) which was first prepared at 1000 ppm (50 mg of TBS in 50 mL of heptane) was stored and the dilutions for 12 different concentrations ranging from 10 ppm-120 ppm were done and day-hold study was performed by determining the absorbance values in the same way by fixing the wavelength at the corresponding $\lambda_{max}$ of the TBS in heptane. Day-hold study data were collected for day 1, 2, 4, 10 and 30 (Table 9). It is observed that the absorbance of the standard solutions at different concentrations showed a significant increase when they were allowed to stand for several days.

TABLE 9

Absorbance of the standard solutions at various concentrations taken on day 1, day 2, day 4, day 10 and day 30

| | Absorbance Concentration of Std. Solution (ppm) | | | | | | | | | | | |
|---|---|---|---|---|---|---|---|---|---|---|---|---|
| Days | 10 | 20 | 30 | 40 | 50 | 60 | 70 | 80 | 90 | 100 | 110 | 120 |
| 1 | 0.18 | 0.37 | 0.54 | 0.72 | 0.93 | 1.12 | 1.33 | 1.53 | 1.76 | 1.97 | 2.19 | 2.43 |
| 2 | 0.26 | 0.46 | 0.62 | 0.75 | 1.11 | 1.24 | 1.51 | 1.66 | 2.00 | 2.09 | 2.31 | 2.55 |
| 4 | 0.33 | 0.64 | 0.71 | 0.81 | 1.28 | 1.57 | 1.67 | 1.84 | 2.28 | 2.18 | 2.45 | 2.67 |
| 10 | 0.39 | 0.58 | 0.80 | 0.84 | 1.32 | 1.63 | 1.80 | 2.02 | 2.51 | 2.29 | 2.69 | 2.71 |
| 30 | 0.45 | 0.69 | 1.06 | 1.30 | 1.81 | 1.90 | 2.06 | 2.39 | 2.64 | 2.77 | 2.99 | 3.29 |

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

In various other embodiments, the invention can also be used for the removal of wax deposition in refinery process equipment, process flow lines, and upgradation of wax.

What is claimed is:

1. A method of processing petroleum hydrocarbons, said method comprising:
   a) dissolving petroleum hydrocarbons in a selected solvent to form a first solution;
   b) measuring absorbance of the first solution;
   c) adding an ionic liquid to the first solution and blending to form a second solution;
   d) measuring absorbance of the second solution;
   e) determining an increase in absorbance of the second solution over the first solution to be at least about 70%;
   f) repeating steps a) to e) for a plurality of solvents and ionic liquids;
   g) selecting at least one solvent and one ionic liquid based on the determination in step e); and
   h) processing the petroleum hydrocarbons using the selected solvent and the ionic liquid in combination;
   wherein the ionic liquid is chosen from: 1,3-dimethylimidazolium 1,1,1-trifluoro-N-[(trifluoromethyl) sulfonyl] methane-sulfonamide; 1-butyl-1-methylpyrrolidinium 1,1,1-trifluoro-N-[(trifluoromethyl)-sulfonyl] methanesulfonamide; diethylammonium phosphate; diethylammonium sulfate; triethylammonium phosphate; triethylammonium sulfate; tripropylammoniumsulfate; tributylammoniumsulfate; 1-butyl-3-methylimidazolium 1,1,1-trifluoro-N-[(trifluoromethyl)sulfonyl] methanesulfonamide; 1-butyl-3-methyl imidazolium chloride; 1-butyl-3-methylimidazolium hexafluorophosphate; 1-ethyl-3-methylimidazolium ethyl sulfate; 1-hexyl-3-methylimidazolium hexafluorophosphate; 1-decyl-3-methylimidazolium bis(trifluoromethyl sulfonyl) imide; 1-octyl-3-methylimidazolium chloride; 1-hexyl-3-methylimidazolium hydrogen sulfate; triethylammoniumtetrafluoroborate; triethylammonium acetate; and mixtures thereof.

2. The method according to claim 1, wherein the absorption is measured using a spectroscopic technique selected from UV-Vis spectroscopy, Fourier transform-infrared spectroscopy and $^{13}$C-nuclear magnetic resonance.

3. The method according to claim 1, further comprises performing hold-time study using the selected solvent and ionic liquid in combination for the solubilization of petroleum hydrocarbons is at least about 60% to about 230%.

4. The method according to claim 1, wherein the petroleum hydrocarbon sources include tank bottom sludge (TBS) and heavy crude oil.

5. The method according to claim 1, wherein the solvent is chosen from aromatic hydrocarbon solvents, aliphatic hydrocarbon solvents, or mixtures thereof.

6. The method according to claim 5, wherein the aliphatic hydrocarbon is pentane, hexane, heptane, octane, decane, ethyl acetate or mixtures thereof.

7. The method according to claim 5, wherein the aromatic hydrocarbon solvent is benzene, ethyl benzene, xylene, phenol, toluene, and mixtures thereof.

* * * * *